US010695798B2

(12) United States Patent
Charrel et al.

(10) Patent No.: US 10,695,798 B2
(45) Date of Patent: Jun. 30, 2020

(54) METHOD FOR ADJUSTING OPERATING PARAMETERS FOR THE POWER SUPPLY OF A TRANSDUCER

(71) Applicant: EYE TECH CARE, Rillieux-la-Pape (FR)

(72) Inventors: Thomas Charrel, Mionnay (FR); Laure Baffie, Miribel (FR)

(73) Assignee: EYE TECH CARE, Rilliex-la-Pape (FR)

( * ) Notice: Subject to any disclaimer, the term of this patent is extended or adjusted under 35 U.S.C. 154(b) by 353 days.

(21) Appl. No.: 15/571,722

(22) PCT Filed: May 9, 2016

(86) PCT No.: PCT/EP2016/060347
§ 371 (c)(1),
(2) Date: Nov. 3, 2017

(87) PCT Pub. No.: WO2016/177910
PCT Pub. Date: Nov. 10, 2016

(65) Prior Publication Data
US 2019/0054499 A1  Feb. 21, 2019

(30) Foreign Application Priority Data

May 7, 2015 (FR) ..................... 15 54143

(51) Int. Cl.
*A61N 7/02* (2006.01)
*B06B 1/02* (2006.01)
(Continued)

(52) U.S. Cl.
CPC ............ *B06B 1/0269* (2013.01); *A61F 9/007* (2013.01); *A61N 7/02* (2013.01); *B06B 1/02* (2013.01);
(Continued)

(58) Field of Classification Search
CPC . A61B 2017/00084; A61B 2017/00725; A61F 9/007; A61N 7/02; B06B 1/02; B06B 1/0269; B06B 1/0607; B06B 2201/76
See application file for complete search history.

(56) References Cited

U.S. PATENT DOCUMENTS 5,460,595 A    10/1995  Hall et al.
2003/0163066 A1  8/2003  Lidgren
(Continued)

FOREIGN PATENT DOCUMENTS

DE    195 10 144      7/1996
WO    WO 97/06766     2/1997
(Continued)

OTHER PUBLICATIONS

Randy King & al; Development and Characterizationo of a Tissue-Mimicking Material for High-Intensity Focused Ultrasound; IEEE Translactions on Ultrasonics, Ferroelectrics, and Frequencey Control vol. 58 No. 7 Jul. 11 pp. 1397-1405.
(Continued)

*Primary Examiner* — Michael F Peffley
(74) *Attorney, Agent, or Firm* — Womble Bond Dickinson (US) LLP (57) ABSTRACT

The invention relates to a method for calibrating a treatment probe comprising at least one cylindrical transducer for generating high-intensity focused ultrasound in a target focus point, the probe being designed to be electrically connected to a power supply source for supplying an electrical signal for the power supply of the transducer, characterised in that the method comprises a step (20) of adjusting a frequency of the electrical signal for the power supply of the transducer in such a way that the variation between the maximum vibration intensity and the minimum vibration intensity of the transducer along the width thereof is minimal.

9 Claims, 3 Drawing Sheets

(51) Int. Cl.
  *A61F 9/007* (2006.01)
  *B06B 1/06* (2006.01)
  *A61B 17/00* (2006.01)

(52) U.S. Cl.
  CPC .. *B06B 1/0607* (2013.01); *A61B 2017/00084* (2013.01); *A61B 2017/00725* (2013.01); *B06B 2201/76* (2013.01)

(56) References Cited

U.S. PATENT DOCUMENTS

2004/0082857 A1\* 4/2004 Schonenberger .... A61B 8/4438
  600/439
2013/0066240 A1\* 3/2013 Van Heesch ............. A61N 7/02
  601/2
2014/0024975 A1\* 1/2014 Little ....................... A61N 7/02
  601/3

FOREIGN PATENT DOCUMENTS

WO  WO 2009/103721  8/2009
WO  WO 2011/148314  12/2011

OTHER PUBLICATIONS

International Search Report PCT/EP2016/060347 dated Aug. 3, 2016 (English translation).

\* cited by examiner

METHOD FOR ADJUSTING OPERATING PARAMETERS FOR THE POWER SUPPLY OF A TRANSDUCER

THE FIELD OF THE INVENTION

The present invention relates to the general technical field of devices and of processing methods for a pathology, such as an eye pathology, by using the so-called technique of high-intensity focused ultrasound (HIFU).

BACKGROUND OF THE INVENTION

Different methods and devices are known, based on the HIFU technology for treating a pathology.

The document WO 2009/103721 notably describes a device for treating an eye pathology including a probe consisting of a ring and of means for generating ultrasound.

The ring has a proximal portion intended to be in contact with an eye of a patient, and a distal portion intended to receive the means for generating ultrasound.

The means for generating ultrasound have a concave profile. More specifically, the means for generating ultrasound comprise six transducers in the form of a cylinder segment positioned on a cylindrical crown of axis A-A'. The means for generating ultrasound also comprise an electric cable intended to be connected to an electric power supply source for allowing supply of energy of the transducers.

The principle for using such a device is the following. Once the probe has been set into place on the organ to be treated, the electric power supply is activated. The transducers begin to vibrate and generate ultrasound which is focused on a target area, inducing its rise in temperature, notably causing coagulation of the tissues heated at this target area.

At each treatment, a used probe may be replaced with a new probe.

Now, the performances of the probes may vary from one probe to another, notably because of the mechanical plays during the assembling of the transducers and/or of the manufacturing tolerances (variations of the surface roughness or of the thickness of each transducer, etc.).

Thus, the temperature attained in the target area may vary between two successive probes (and even between two transducers of a same probe).

This why it is necessary to calibrate each transducer of a probe for determining the energy to applied to it according to the desired temperature in the target area to be treated.

This desired temperature may vary depending on the type of treatment which one wishes to carry out. For example, for each treatment of an organ, it may be preferable to induce a low increase in the temperature during a significant time so as to cause a "slow coagulation" of the target area; while for other treatments, a significant increase in the temperature during a short time will be preferred so as to cause a "fast coagulation" of the target area.

This desired temperature may also vary according to the target area or to the organ to be treated. For example, the desired temperature will be different in the case of a treatment of the ciliary body relatively to the treatment of liver cancer cells.

It is therefore necessary:
on the one hand to define calibration parameters of the probes according to the targeted application, and
on the other hand, to calibrate each transducer of a probe before its use.

An object of the present invention is to propose a solution for adjusting supply parameters of a probe for treating a pathology based on the HIFU technique.

SHORT DESCRIPTION OF THE INVENTION

For this purpose, the invention proposes a method for calibrating a treatment probe including at least one transducer intended to generate high-intensity focused ultrasound in a target focusing area, the probe being intended to be electrically connected to a power supply source for providing an electric power supply signal of the transducer, remarkable in that the method comprises a step for adjusting a frequency of the electric power supply signal of the transducer so that the variation between the maximum vibration intensity and the minimum vibration intensity of the transducer along its width is a minimum.

Preferred aspects but non-limiting aspects of the method according to the invention are the following:
the step for adjusting the excitation frequency of the transducer may comprise the sub-steps of:
supplying the transducer with a plurality of input signals having equal amplitudes and different respective frequencies,
measuring temperatures (/pressures) in different points of the target area for each input signal,
obtaining a temperature profile (/pressure) of the transducer for each input signal,
selecting from among the plurality of temperature profiles (/pressure) of the transducer, the temperature profile (/pressure) for which the variation between the maximum temperature (/pressure) and the minimum temperature (/pressure) of the temperature profile (/pressure) is the smallest along the width of the transducer,
calculating the frequency of the electric power supply signal of the transducer from the frequency of the input signal associated with the selected temperature profile (/pressure);
the method may further comprise a step for determining a resonance frequency of the transducer;
the frequencies of a plurality of input signals may be comprised between 90% and 110% of the resonance frequency of the transducer;
the method may further comprise a step for adjusting a voltage of the power supply electric signal of the transducer according to a set temperature in the target focusing area;
the step for adjusting an excitation voltage may comprise the sub-steps of:
a) supplying the transducer with an input signal with a fixed frequency, notably equal to the excitation frequency,
b) measuring temperatures in different points of the target focusing area,
c) calculating an average temperature from the measured temperatures,
d) comparing the calculated average temperature with the set temperature,
e) if the average temperature is greater than the set temperature, then reducing the amplitude of the input signal and repeating the operations b) to e),
f) if the average temperature is less than the set temperature, then increasing the amplitude of the input signal and repeating the operations b) to f), g) if the average temperature is equal to the set temperature, selecting as an excitation voltage the value of the voltage of the input signal.

The invention also relates to a probe for treating a pathology including means for generating ultrasound including at least one transducer for generating high-intensity focused ultrasound in a target focusing area, the probe being intended to be electrically connected to a power supply source for providing an electric power supply signal of the transducer, remarkable in that the probe comprises adjustment means adapted for adjusting the frequency of the electric power supply signal of the transducer so that the variation between the maximum vibration intensity and the minimum vibration intensity of the transducer along its width is a minimum.

Advantageously, the adjustment means may comprise an electronic card for controlling the power supply source, said card including a memory containing at least one calibration parameter obtained by applying the calibration method described above.

Preferably, the electronic control card is integrated into the means for generating ultrasound.

SHORT DESCRIPTION OF THE DRAWINGS

Other advantages and features of the method according to the invention and of the associated product will become better apparent from the description which follows of several embodiments, given as non-limiting examples, from the appended drawings wherein.

DETAILED DESCRIPTION OF THE INVENTION

Examples of a device and of the method according to the invention will now be described in more details with reference to the figures. In these different figures, equivalent elements are designated by the same numerical reference.

1. A Device for Treating a Pathology

Figure 1:
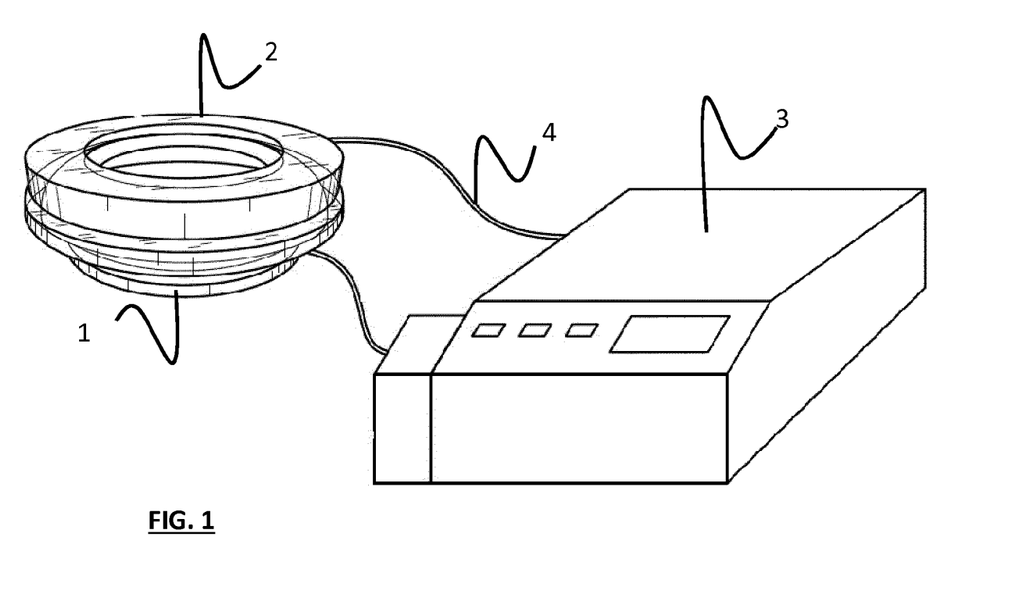
FIG. 1 schematically illustrates a treatment device

An example of a device based on the HIFU technology for treating an eye pathology is illustrated in FIG. 1.

The device comprises a support 1 for the means for generating ultrasound 2 electrically connected to an electric power supply source 3 via an electrically conductive cable of any type known to one skilled in the art.

The support is in the form of a ring which is particularly adapted for the treatment of an eye pathology. Of course, this device may be adapted for allowing the treatment of other organs that the eye, notably by modifying the shape of the support 1 and/or the layout of the means for generating ultrasound 2.

The electric power supply source 3 is adapted for delivering electric oscillations to the means for generating ultrasound. These electric oscillations may be delivered in a continuous mode (i.e. permanent electric oscillations) or in a cyclic mode (i.e. a succession of periods, one period including a first time interval including one (or several) electric oscillation(s) and a second time interval not comprising any electric oscillation). In other words, the generator is adapted for generating one (or several) trains of electric pulses. Preferably, the electric power supply source 3 is used in a continuous mode for increasing the effect of heating up the targeted tissues (as compared with a power supply source used in a cyclic mode for example).

The means for generating ultrasound 2 give the possibility of generating ultrasonic energy. They are positioned in a way adapted to the pathology to be treated. For the treatment of an eye pathology, they comprise a ring-shaped crown including:

first and second opposite bases, an external side wall between the first and second bases, and an internal side wall defining a central channel between the first and the second bases.

The first base includes at least one transducer having a radiating element for generating ultrasound.

The profile of the radiating element(s) may be adapted for giving the possibility of orienting and focusing the ultrasound on a given targeted area corresponding to a line segment, as this will be described in more detail subsequently.

Alternatively, the transducer may comprise one or more reflectors for reflecting, orienting and focusing in a given targeted area the ultrasound generated by the radiating element (or elements).

In an embodiment, six transducers extend over the first base of the crown. The transducers are grouped in two pairs of three transducers separated by two inactive sectors. The inactive sectors are localized on the crown so as to extend in a temporal/nasal plane of the patient when the probe is placed on the eye, these sectors corresponding to areas of the eye including the majority of the nerve and vascularity terminations.

The means for generating ultrasound may also comprise an electronic card for controlling the power source supplying the means for generating ultrasound.

This card comprises a memory in which are stored operating parameters for each transducer. These operating parameters give the possibility of controlling the power supply source according to the technical characteristics associated with each transducer.

Indeed, from the fact that the manufacturing tolerances of the probes (dimensional, geometrical, machining tolerances, etc.), two transducers supplied with identical electric voltage and frequency may have different acoustic responses.

Notably, the resonance frequency of each transducer may vary from a few tens of percent from one transducer to the other. Also, the yield and/or the acoustic response of each transducer may vary from one transducer to the other. Thus, it may be necessary to adjust the voltage and the applied frequency to each transducer of a probe so as to homogenize their effect at their respective target areas.

The electronic card gives the possibility of controlling:

an electric operating current, an electric operating frequency and/or an operating frequency applied to each transducer of a probe by the power supply source so as to homogenize the thermal responses of said transducers to the levels of their respective target areas (i.e. areas for focusing the ultrasound).

In certain embodiments, the electronic card is implanted in the power supply source 3. In this case, the operating parameters of the transducers of a probe have to be inputted in the power supply source 3 for each change of probe.

In other embodiments, the electronic card is integrated into each probe, for example housed in the crown. This gives the possibility of having a totally calibrated probe without requiring the application of any operation for adjusting the power supply source 3 by the user. The risks of error are thereby limited and the use of the treatment device is simplified.

2. Method for Adjusting the Operating Parameters of a Probe

An exemplary method for adjusting the operating parameters of a probe will now be described.

This method gives the possibility for each transducer of a probe of determining the operating parameters recorded in the memory of the electronic card for the treatment of a tissue.

The adjustment method comprises steps carried out on a test bench for determining an optimum excitation frequency and an optimum excitation voltage for each transducer.

2.1. Determination of the Rated Frequency of Each Transducer

Figure 2:
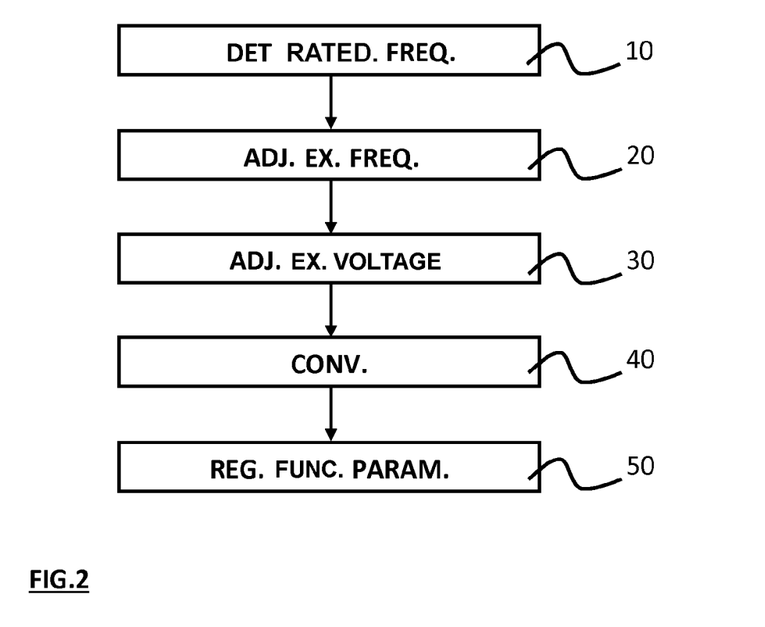
FIG. 2 schematically illustrates a method for adjusting operating parameters of a treatment probe.

With reference to FIG. 2, the adjustment method comprises a step 10 consisting in determining the rated frequency (or resonance frequency) of each transducer of a probe.

Each transducer consists of a piezo-electric material able to vibrate when it is subject to an electric voltage of a given frequency. These vibrations are then able to be sustained, the resonance frequency of the transducer is attained (maximum vibration) to be transmitted to the surrounding medium in the form of ultrasound.

The rated frequency of a transducer may for example be determined according to the following method. The transducer is connected to a network analyzer which gives the possibility of measuring an electric impedance on a given frequency range.

The rated frequency then corresponds to the electric frequency for which the impedance matching is optimum (i.e. the electric frequency for which the vibration is maximum) which is expressed electrically by a ratio between a received electric signal divided by a minimum emitted electric signal.

For a probe including six transducers, the determination step will be applied six times for determining the rated frequency of each respective transducer.

2.2. Adjustment of the Excitation Frequency

The method further comprises a step 20 for adjusting the excitation frequency of each transducer about its rated frequency.

The adjustment of the excitation frequency of a transducer allows a more homogeneous distribution of the acoustic energy which it produces over the whole of its width L (corresponding to the generatrix of the cylinder portion making up the transducer).

Figure 3:
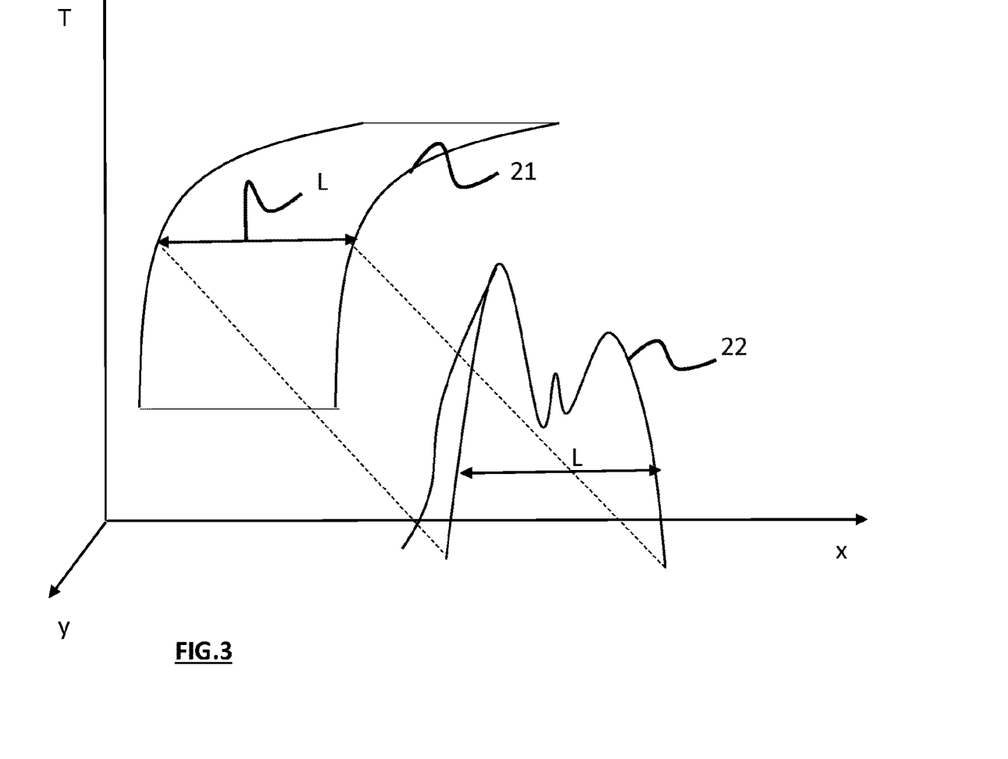
FIG. 3 illustrates a vibration profile of a transducer.

Indeed, and as shown by the vibration profile 22 illustrated in FIG. 3, a transducer 21 does not vibrate uniformly over the whole of its width L so that the lesion sizes generated by two transducers of same dimensions may vary.

For a given transducer, the adjustment of the excitation frequency consists of:
  connecting the transducer to a (voltage) generator for applying an input voltage (i.e. sinusoidal voltage) to the transducer,
  positioning a temperature measurement device—such as a thermocouple—in the target area of the transducer.

The frequency of the input signal is varied in a range of values around the rated frequency of the transducer (±10% of the rated frequency), for example in a frequency range comprised between minimum and maximum frequencies such as:
  the minimum frequency is equal to 90% of the rated frequency,
  the maximum frequency is equal to 110% of the rated frequency.

The measurement device gives the possibility of obtaining a temperature profile for each input signal of different frequency. This temperature profile is representative of the vibration profile of the transducer.

The frequency of the input signal for which the variation between the maximum temperature and the minimum temperature of the temperature profile is the smallest is then selected as an excitation frequency.

Figure 4:
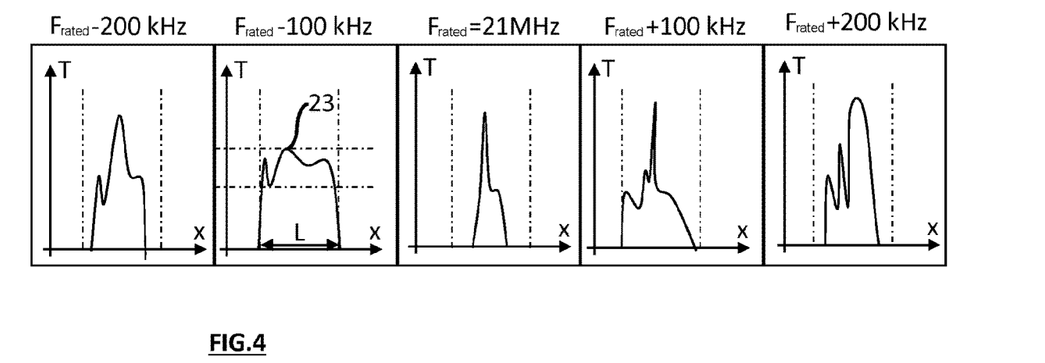
FIG. 4 illustrates a sequence of temperature profiles obtained for input signals of variable frequency.

For example, with reference to FIG. 4 illustrating a profile variation of temperature of a transducer for an input signal for which the frequency varies from ±200 kHz around the rated frequency (21 MHz) of the transducer, the rated frequency minus 100 kHz will be selected as an excitation frequency. Indeed, for this excitation frequency, the temperature profile 23 is more homogeneous over the whole width of the transducer (and therefore of the target area).

The step for adjusting the excitation frequency of a transducer gives the possibility of obtaining the temperature profile of the more homogenous target area.

During this step for adjusting the excitation frequency, the voltage of the input signal is maintained constant.

Another step of the method will consist in adjusting the excitation voltage of each transducer for attaining a set temperature at the target area.

For a probe including six transducers, the adjustment step will be applied six times in order to determine an excitation frequency for each respective transducer.

2.3. Adjustment of the Excitation Voltage

Another step 30 of the method consists of adjusting the applied excitation voltage to each transducer by the power supply source.

As indicated earlier, the yields of the transducers may vary from one transducer to the other. Thus, the excitation voltage has to be adjusted for each transducer so that the transducers of a probe deliver identical amounts of acoustic energy at their respective target areas.

Indeed, even if the step for adjusting the excitation frequency gives the possibility of uniformizing the temperature profile (and therefore the vibration profile) of each transducer of a probe, the profiles of the different transducers of a probe however have differences between them. Now, the temperature in the target area of a transducer depends on its vibration profile.

It is therefore necessary to adjust the excitation voltage of each transducer so that:
  the temperature attained at the target area corresponds to a set temperature, and for which
  the attained temperatures in the respective target areas of the different transducers of a probe are substantially identical.

For a given transducer, the adjustment of the excitation voltage consists of connecting the transducer to a (voltage) generator for applying an input signal (i.e. a sinusoidal voltage) to the transducer, and to position a device for measuring temperature—such as a thermocouple—in the target area of the transducer.

The voltage of the input signal is then varied until the temperature at the target area corresponds to the set temperature.

In certain alternative embodiments, an average temperature is considered over the target area for adjusting the excitation voltage of a transducer.

More specifically, for a given voltage input signal:
the temperatures are measured in different points of the target area;
the average temperature is calculated from the measured temperatures;
this average temperature is compared with a set temperature;
the voltage of the input signal is decreased (respectively increased) if the average temperature is greater (respectively smaller than) the set temperature;
the excitation voltage is assigned the value of the voltage of the input signal if the average temperature is equal to the set temperature.

In other alternatives, the average temperature is considered at half-height over the target area. This gives the possibility of limiting the influence of the temperature peaks in the adjustment of the excitation voltage.

For a probe including six transducers, the adjustment step will be applied six times in order to determine an excitation voltage for each respective transducer.

2.4. Recording the Operating Parameters

At the end of the determination and adjustment steps, for each transducer of a probe, an excitation frequency and an excitation voltage are obtained.

They are obtained by using a test bench including:
a support for the positioning of the means for generating ultrasound,
a base intended for receiving a block of thermosensitive gel used for simulating the tissue intended to be treated,
a thermocouple intended to be introduced into the block of gel at the target area of each transducer for measuring temperatures in different points of the target area.

Preferably, the block of gel is a gel based on animal protein, and more specifically based on "BSA" ("Bovine Serum Albumine"). Such a gel is notably described in the publication entitled "Gel phantom for use in high-intensity focused ultrasound dosimetry" of C. Lafon, Zderic V, Noble M L, Yuen J C, Kaczkowski P J, Sapozhnikov O A, Chavrier F, Crum L A, Vaezy S published in Ultrasound Med. Biol. 2005 Oct. 31, Vol. 31 (No. 10): pages 1383-1389.

An example of a composition of the gel is given as an indication in the following table.

| COMPOSITION | PROPORTION |
| --- | --- |
| Degassed water (mL) | 143.08 |
| Acrylamide/Bis-acrylamide 40%(mL) | 34.92 |
| TRIS 1 mol/L)(mL) | 20 |
| BSA (g) | 36 |
| 10% APS (mL) | 1.68 |
| TEMED (mL) | 0.2 |

With:
TRIS is trishydroxymethylaminomethane, wherein 1 L TRIS 1 mol/L=88.8 g TRIZMA Hydrochloride+53 g of basic TRIS+1 L of water,
TEMED, tetramethylethylenediamine, and
APS, ammonium persulfate, wherein 10 mL of 10% of APS=1 g APS+10 mL of water.

The characteristics of this thermosensitive gel have the advantage of being representative of the characteristics of a tissue.

Nevertheless, the estimated excitation voltage on the test bench (for the set temperature) has to be transposed (step 40) for a use of the probe with the power supply source (the latter has a characteristic impedance different from that of the generator used on the test bench).

For this purpose, a transfer function is applied to the excitation voltage.

The operating parameters (frequency/transposed voltage) associated with each transducer are recorded (step 50) in the memory of the electronic card for allowing control of the power supply source 3 in order to obtain:
for each transducer, a substantially homogeneous heating of the whole surface of its target tissue area,
for the different transducers, substantially homogeneous heating processes of the different target tissue areas.

3. Method for Determining One (or Several) Calibration Parameters of a Treatment Probe Depending on a Targeted Application.

It was seen earlier that the adjustment method gives the possibility of uniformizing the profiles of the vibrations generated by the transducers of a probe in their respective target tissue areas.

If the probe is oriented towards a tissue, these vibrations give the possibility of heating the tissue at the target tissue areas.

Now, the required temperature (hereafter designated as "desired temperature") may vary from one tissue to the other.

The same applies to the required period for efficiently treating a tissue which may vary depending on the treatment to be applied or on the treatment to be carried out (hereafter designated as "desired period").

Thus, the efficiency of a treatment depends on a desired temperature/desired period pair. From the selection of this pair, depends the set temperature used in the adjustment method described in point 2.

The inventors have ascertained a correlation between the temperature rise kinetics observed in a gel—based on bovine serum albumine and notably for the gel given in the table above—at the target area of a transducer depending on the acoustic intensity of said transducer, this acoustic intensity itself depending on the set temperature used for calibrating the transducer.

In order to allow rapid determination of a set temperature according to a desired temperature and/or a desired period for a treatment, the inventors have estimated different curves by using a test bench. More specifically, the inventors selected a transducer as a reference standard depending on certain quality criteria (mechanical properties of the transducer and/or the quality of the lesion generated by the transducer, etc.)

The inventors then:
calibrated the reference standard in voltage for different set temperatures; and then,
for each set temperature, measured the variation of the temperature in the target area versus time.

Figure 5:
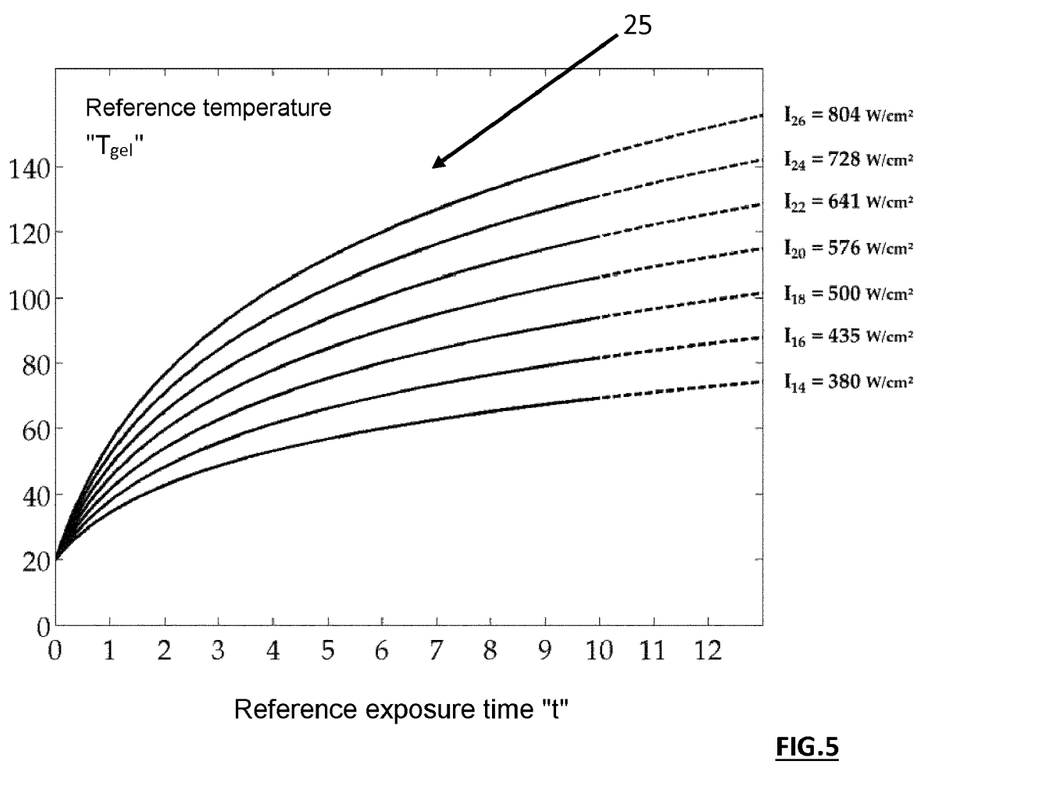
FIG. 5 is an abacus of representative curves of a temperature in a gel depending on an exposure duration to ultrasound.

The inventors thereby obtained a plurality of curves illustrated on an abacus represented in FIG. 5, each curve being associated with a respective set temperature.

For example, the inventors determined a first excitation voltage to be applied to the transducer forming the reference standard so that the temperature in the target area increases by a predetermined temperature (for example 14° C.) after a predetermined period (for example half a second). And then the inventors measured the variation of the temperature in the target area versus time over a time period (for example comprised between 0 seconds and 30 minutes). They thereby obtained the curve referenced as $I_{14}$ on the abacus of FIG. 5.

The inventors then determined a second excitation voltage to be applied to the transducer forming the reference standard so that the temperature in the target area increases by a temperature (for example 16° C.) after a half a second). Once the transducer standard calibrated, the inventors measured the variation of the temperature in the target area versus time over a time period comprised between 0 seconds and 30 minutes. They thereby obtained the curve referenced as $I_{16}$ on the abacus of FIG. 5. And so forth.

This gave the possibility of resulting with the abacus illustrated in FIG. 5. This abacus consists of curves each illustrating a temperature in a gel depending on an exposure period to ultrasound, said curves each being associated with a respective set temperature (which may be used in the adjustment method described in point 2). Actually, FIG. 5 illustrates the time-dependent in a temperature difference in a thermosensitive gel versus time for set temperatures comprised between 14° C. and 26° C.

As indicated above, the characteristics of this thermosensitive gel have the advantage of being representative of the characteristics of a tissue, so that there exists a correlation between;
- the desired temperature in a tissue and the temperature in the gel
- the desired exposure period in a tissue and the exposure period in the gel.

Thus, these curves give the possibility indirectly of setting up a relationship between a set temperature depending on a desired time and on a desired exposure period for obtaining an efficient treatment in a tissue.

The thermal relationship which governs the curves illustrated in FIG. 5 may be interpolated by a logarithmic law of the type:

$$T_i(t,K) = \log(t+1) \times K_i + T_{room};$$

With:
"t" a treatment duration (or insonication time) varying from 0 to +inf,
"$T_{room}$" room temperature (here 20° C.) and
"$K_i$" a weighting coefficient related to acoustic intensity.

The following table gives the values obtained for the gel described in the previous table:

| I (or set temperature) | Iac (acoustic intensity in W/cm²) | ΔTmax Thermocouple at 6 s (° C.) | $K_i$ (° C./s) |
|---|---|---|---|
| 14 | 380 | 40 | 47.33 |
| 16 | 435 | 50 | 59.16 |
| 18 | 500 | 60 | 80.00 |
| 20 | 576 | 70 | 82.83 |
| 22 | 641 | 80 | 94.66 |
| 24 | 728 | 90 | 106.50 |
| 26 | 804 | 100 | 118.33 |

The operating principle of this abacus is the following. When a user wishes to calibrate a probe for a particular treatment, he/she determines a desired temperature and a desired exposure period guaranteeing the efficiency of the treatment of the tissue.

He/She then estimates a reference temperature in the gel and a reference exposure period in the gel from desired reference temperatures and periods (for example by applying a transfer function to the desired temperatures and periods).

By transferring the estimated reference temperature and the estimated exposure period onto the abacus of FIG. 5, a set temperature is inferred therefrom which may be used in the adjustment method described in point 2.

Of course, one skilled in the art will be able to reproduce the same test with a different gel by resuming the method described earlier.

The reader will have understood that many modifications may be brought to the invention described earlier without departing materially from the new teachings and advantages described here.

For example, in the embodiments described earlier, the electric cable intended to be connected to an electric power supply source for allowing the energy supply of the transducers is integrated to the probe. Alternatively, this electric cable may be integrated to the power supply source, the probe comprising an electric connection connector for allowing it to be connected to the electric cable.

Also, in the preceding description, the gel used was a thermosensitive gel based on proteins. Of course, the thermosensitive gel used may be any other synthetic gel or material for which the behaviour is representative of a tissue when it is subject to radiation for increasing its temperature.

Moreover, in the preceding description, the step for adjusting the excitation frequency of the transducer was achieved by obtaining temperature profiles of the transducer for different input signals. Alternatively, the adjustment step may be achieved by obtaining pressure profiles for different input signals for supplying the transducer.

Therefore, all the modifications of this kind are intended to be incorporated inside the scope of the appended claims.

The invention claimed is:

1. A method for calibrating a treatment probe including at least one transducer for generating high-intensity focused ultrasound in a target focusing area, the probe being intended to be electrically connected to a power supply source for providing an electric power supply signal of the transducer,
wherein the method comprises a step for adjusting an excitation frequency of the electric power supply signal of the transducer so that the variation between the maximum vibration intensity and the minimum vibration intensity of the transducer along its width is a minimum.

2. The calibration method according to claim 1, wherein the step for adjusting the excitation frequency of the transducer comprises the sub-steps of:
supplying the transducer with a plurality of input signals having equal amplitudes and different respective frequencies,
measuring temperatures in different points of the target focusing area for each input signal,
obtaining a temperature profile of the transducer for each input signal,
selecting from among the plurality of temperature profiles of the transducer, the temperature profile for which the variation between the maximum and the minimum of the temperature profile is the smallest along the width of the transducer,
calculating the excitation frequency of the electric power supply signal of the transducer from the frequency of the input signal associated with the selected temperature profile.

3. The calibration method according to claim 1, which further comprises a step for determining a resonance frequency of the transducer.

4. The calibration method according to claim 2, which further comprises a step for determining a resonance frequency of the transducer, wherein the frequencies of a plurality of input signals are comprised between 90% and 110% of the resonance frequency of the transducer.

5. The calibration method according to claim 1, which further comprises a step for adjusting a voltage of the power supply electric signal of the transducer according to a set temperature in the target focusing area.

6. The calibration method according to claim 5, wherein the step for adjusting an excitation voltage, comprises the sub-steps of:
   a) supplying the transducer with an input signal with a fixed frequency, notably equal to the excitation frequency,
   b) measuring temperatures in different points of the target focusing area,
   c) calculating an average temperature from the measured temperatures,
   d) comparing the calculated average temperature with the set temperature,
   e) if the average temperature is greater than the set temperature, then reducing the amplitude of the input signal and repeating the operations b) to e),
   f) if the average temperature is less than the set temperature, then increasing the amplitude of the input signal and repeating the operations b) to f),
   g) if the average temperature is equal to the set temperature, selecting as an excitation voltage the value of the voltage of the input signal.

7. A probe for treating a pathology including means for generating ultrasound including at least one transducer for generating high-intensity focused ultrasound in a target focusing area, the probe being intended to be electrically connected to a power supply source for providing an electric power supply signal of the transducer, wherein the probe comprises adjustment means adapted for adjusting an excitation frequency of the electric power supply signal of the transducer so that the variation between the maximum vibration intensity and the minimum vibration intensity of the transducer along its width is a minimum.

8. The probe according to claim 7, wherein the adjustment means comprise an electronic card for controlling the power supply source, said card including a memory containing at least one calibration parameter.

9. The probe according to claim 8, wherein the electronic control card is integrated into the means for generating ultrasound.

* * * * *